(12) United States Patent
Hsu et al.

(10) Patent No.: US 11,672,443 B2
(45) Date of Patent: Jun. 13, 2023

(54) JOINT BENDING STATE DETERMINING DEVICE AND METHOD

(71) Applicant: Wistron Corp., New Taipei (TW)

(72) Inventors: Chunpeng Hsu, New Taipei (TW); Hsin-Hui Liao, New Taipei (TW); Yi-Sheng Kao, New Taipei (TW); Tsung-Yu Tsai, New Taipei (TW); Tai-Yun Chen, New Taipei (TW)

(73) Assignee: WISTRON CORP., New Taipei (TW)

( * ) Notice: Subject to any disclaimer, the term of this patent is extended or adjusted under 35 U.S.C. 154(b) by 403 days.

(21) Appl. No.: 16/815,360

(22) Filed: Mar. 11, 2020

(65) Prior Publication Data

US 2021/0145322 A1 May 20, 2021

(30) Foreign Application Priority Data

Nov. 20, 2019 (TW) .................................. 108142162

(51) Int. Cl.
*A61B 5/11* (2006.01)
*G01B 21/22* (2006.01)
(Continued)

(52) U.S. Cl.
CPC .......... *A61B 5/1121* (2013.01); *A61B 5/1071* (2013.01); *A61B 5/1126* (2013.01);
(Continued)

(58) Field of Classification Search
None
See application file for complete search history.

(56) References Cited

U.S. PATENT DOCUMENTS

| 5,313,968 A * | 5/1994 | Logan ................. A61B 5/4528 600/595 |
| 2007/0032748 A1 * | 2/2007 | McNeil ............... A61B 5/1121 600/595 |

(Continued)

FOREIGN PATENT DOCUMENTS

| CN | 208677399 U | 4/2019 |
| FR | 3012315 A1 | 5/2015 |

(Continued)

OTHER PUBLICATIONS

European Search Report in Application No. 20166366.3 dated Oct. 16, 2020.

(Continued)

*Primary Examiner* — Benjamin S Melhus
(74) *Attorney, Agent, or Firm* — Locke Lord LLP; Tim Tingkang Xia, Esq.

(57) ABSTRACT

A joint bending state determining device comprises a sensor group and a processor. The sensor group comprises first and second gravity sensors. The first/second gravity sensor generates a first/second polar angle and a first/second azimuth angle. The processor obtains a first length corresponding to the first gravity sensor and a second length corresponding to the second gravity sensor, obtains a set of coordinates of a joint in a coordinate system according to the first polar angle, the first azimuth angle and the first length, obtains a set of coordinates of the second gravity sensor in the coordinate system according to the set of coordinates of the joint, the second polar angle, the second azimuth angle and the second length, and obtains a joint angle according to the set of coordinates of the second gravity sensor in the coordinate system, the first length and the second length.

15 Claims, 5 Drawing Sheets

(51) Int. Cl.
*A61B 5/107* (2006.01)
*A61B 5/00* (2006.01)

(52) U.S. Cl.
CPC ............ *A61B 5/4528* (2013.01); *G01B 21/22* (2013.01); *A61B 5/0024* (2013.01); *A61B 2562/0219* (2013.01)

(56) References Cited

U.S. PATENT DOCUMENTS

| | | | | |
|---|---|---|---|---|
| 2013/0217352 | A1* | 8/2013 | Pan | G16H 50/30 340/539.12 |
| 2013/0310711 | A1* | 11/2013 | Wang | A61B 5/4528 600/595 |
| 2015/0100141 | A1* | 4/2015 | Hughes | G06K 9/00496 700/92 |
| 2016/0313798 | A1* | 10/2016 | Connor | A61B 5/1125 |
| 2016/0324447 | A1* | 11/2016 | Hallberg | A61B 5/7282 |
| 2017/0361165 | A1* | 12/2017 | Miller | A63B 21/00178 |
| 2018/0271432 | A1* | 9/2018 | Auchinleck | A61B 5/1071 |
| 2019/0101415 | A1* | 4/2019 | Sekeljic | G01D 5/2073 |
| 2020/0046264 | A1* | 2/2020 | Chapman | A61B 5/1071 |
| 2020/0054275 | A1* | 2/2020 | Kim | A61B 5/1071 |
| 2020/0375497 | A1* | 12/2020 | Jin | A61B 5/1126 |
| 2022/0304594 | A1* | 9/2022 | Rehbein | A61B 5/4836 |

FOREIGN PATENT DOCUMENTS

| | | |
|---|---|---|
| TW | 201639528 A | 11/2016 |
| WO | 2018092944 A1 | 5/2018 |
| WO | 2019113441 A1 | 6/2019 |

OTHER PUBLICATIONS

European Patent Office, Oct. 16, 2020, Germany.
Taiwan Patent Office, "Office Action", dated May 1, 2020, Taiwan.

\* cited by examiner

JOINT BENDING STATE DETERMINING DEVICE AND METHOD

CROSS-REFERENCE TO RELATED APPLICATIONS

This non-provisional application claims priority under 35 U.S.C. § 119(a) on Patent Application No(s). 108142162 filed in Taiwan on Nov. 20, 2019, the entire contents of which are hereby incorporated by reference.

BACKGROUND

1. Technical Field

This invention relates to a joint bending state determining device, and particularly to a joint bending state determining device including a number of sensors.

2. Related Art

With the trend of population aging, the proportion of people with joint pain, especially knee pain, is getting higher and higher. In order to relieve joint pain, the hospital often requires patients to perform rehabilitation courses such as joint flexion strengthening, muscle strength training, etc. Besides performed in the hospital, these rehabilitation courses should be performed at home by patients to achieve good rehabilitation outcomes. However, in the case of patients performing the rehabilitation courses without supervision, it is difficult for the patients to determine whether the bending state of the joint conforms to the requirements of the rehabilitation courses.

SUMMARY

Accordingly, this invention provides a joint bending state determining device and a joint bending state determining method.

According to one or more embodiment of this disclosure, a joint bending state determining device comprises a sensor group and a processor. The sensor group comprises first and second gravity sensors. The first gravity sensor is configured to generate a first polar angle and a first azimuth angle. The second gravity sensor is configured to generate a second polar angle and a second azimuth angle. The processor is connected with the sensor group and configured to obtain a first length corresponding to the first gravity sensor and a second length corresponding to the second gravity sensor, to obtain a set of coordinates of a joint in a coordinate system according to the first polar angle, the first azimuth angle and the first length, to obtain a set of coordinates of the second gravity sensor in the coordinate system according to the set of coordinates of the joint, the second polar angle, the second azimuth angle and the second length, and to obtain a joint angle according to the set of coordinates of the second gravity sensor in the coordinate system, the first length and the second length. The first length is associated with a distance between the first gravity sensor and the set of coordinates of the joint, and the second length is associated with a distance between the second gravity sensor and the set of coordinates of the joint.

According to one or more embodiment of this disclosure, a joint bending state determining method comprises obtaining a first length corresponding to the first gravity sensor and a second length corresponding to the second gravity sensor, obtaining a first polar angle and a first azimuth angle generated by the first gravity sensor and a second polar angle and a second azimuth angle generated by the second gravity sensor, obtaining a set of coordinates of a joint in a coordinate system according to the first polar angle, the first azimuth angle and the first length, obtaining a set of coordinates of the second gravity sensor in the coordinate system according to the set of coordinates of the joint, the second polar angle, the second azimuth angle and the second length, and obtaining a joint angle according to the set of coordinates of the second gravity sensor in the coordinate system, the first length and the second length. The first length is associated with a distance between the first gravity sensor and the set of coordinates of the joint, and the second length is associated with a distance between the second gravity sensor and the set of coordinates of the joint.

In view of the above description, the joint bending state determining device and method provided in this invention can perform the procedure for determining the bending state of a joint by merely two sensors. Therefore, the difficulty of charging, storage and wearing of the joint bending state determining device may be reduced, and the device may be lighter. For the joint bending state determining device provided in this invention, the distances respectively between the two sensors and the joint is not limited. Accordingly, the user may freely choose the suitable assistive device or protective gear to dispose the two sensors according to the needs. The joint bending state determining device provided in this invention does not need to be equipped with an exclusive assistive device or protective gear. In addition, the joint bending state determining device may improve the freedom of wearing without restricting the wearing positions of the two sensors.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figure 1:
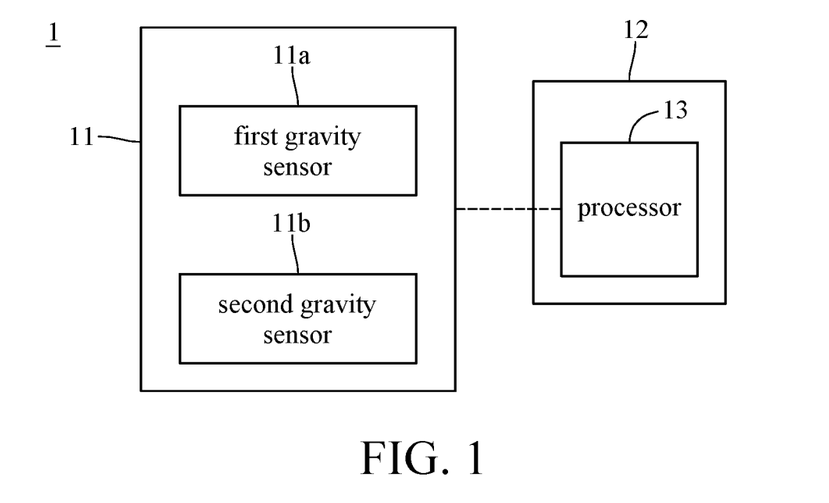
FIG. 1 is a functional block diagram of a joint bending state determining device according to an embodiment of this invention.

Please refer to FIG. 1 that is a functional block diagram of a joint bending state determining device 1 according to an embodiment of this invention. As shown in FIG. 1, the joint bending state determining device 1 comprises a sensor group 11 and a computing device 12. The computing device 12 comprises a processor 13. The sensor group 11 comprises the first gravity sensor (g-sensor) 11a and the second gravity sensor 11b, wherein the first gravity sensor 11a is configured to generate the first polar angle and the first azimuth angle based on its location, and the second gravity sensor 11b is configured to generate the second polar angle and the second azimuth angle based on its location. The first gravity sensor 11a and the second gravity sensor 11b can be respectively disposed on limbs of a human body connected by a joint such as a knee, an elbow, a hip joint, etc. More specifically, the first and second gravity sensors 11a and 11b can be respectively disposed into two separate straps, patches or other assistive devices or protective gear, and fixed to the limbs by means of strapping, sticking, etc.; or, the first and second gravity sensors 11a and 11b can disposed in the same protective gear such as a knee brace, and more particularly at the positions, corresponding to the upper leg (thigh) and the lower leg (calf), of the knee brace. The above setting manners are exemplary. The user may freely choose the suitable assistive device or protective gear to dispose the two sensors according to the needs, and the two sensors do not need to be equipped with an exclusive assistive device or protective gear. In another embodiment, the gravity sensors (the first gravity sensor 11a and the second gravity sensor 11b) are replaced by accelerometers.

The processor 13 is, for example, a central processing unit, a microcontroller, a programmable logic controller, etc. The processor 13 can be connected with the sensor group 11 in a wired or wireless way, and obtain the information corresponding to the locations of the first gravity sensor 11a and the second gravity sensor 11b of the sensor group 11 so as to determine the bending state of a joint, that is, the relationship such as an included angle (hereinafter called "joint angle") between two limbs connected by the joint. The procedure of determining a joint angle will be described later. In an embodiment, the processor 13 can be disposed in a user device such as a computer, a cell phone, a tablet, etc. and comprise a wireless communication component for communicating with the sensor group 11. In another embodiment, the processor 13 can be disposed on the same circuit board as the first gravity sensor 11a or the second gravity sensor 11b, and be electrically connected thereto; or, the processor 13 and one of the first and second gravity sensors 11a and 11b can be disposed in the same assistive device and have an electrical connection or a communication connection with each other, and the processor 13 can have a communication connection with the other one of the first and second gravity sensors 11a and 11b.

More particularly, the joint bending state determining device 1 can further comprise an input interface that has an electrical connection or a communication connection (wired communication or wireless communication) with the processor 13. The input interface is, for example, a touch screen, a keyboard, a microphone, etc., and can provide a platform for a user to input specific information corresponding to the first and second gravity sensors 11a and 11b. Moreover, the joint bending state determining device 1 can further comprise an output interface that has an electrical connection or a communication connection with the processor 13. The output interface is, for example, a display screen, a loudspeaker, etc., and can provide a user with the determined result of the bending state of a joint. In addition, the joint bending state determining device 1 can further comprise a memory electrically connected with the processor 13, or the processor 13 can have a communication connection with a cloud database. The processor 13 can record the determined result of the bending state of a joint in the memory or the cloud database. In this way, the doctor or physical therapist can determine the rehabilitation progress or joint recovery state of the user (a patient with joint pain) according to the record of the joint bending state of the use. In an embodiment, the aforementioned input interface/output interface/memory can be the component disposed in a user device. In another embodiment, the assistive device where the first gravity sensor 11a or the second gravity sensor 11b is disposed can further comprise the input interface/output interface/memory. In yet another embodiment, the assistive device where the first gravity sensor 11a is disposed and the assistive device where the second gravity sensor 11b is disposed can each have an input interface/output interface/ memory.

Figure 2:
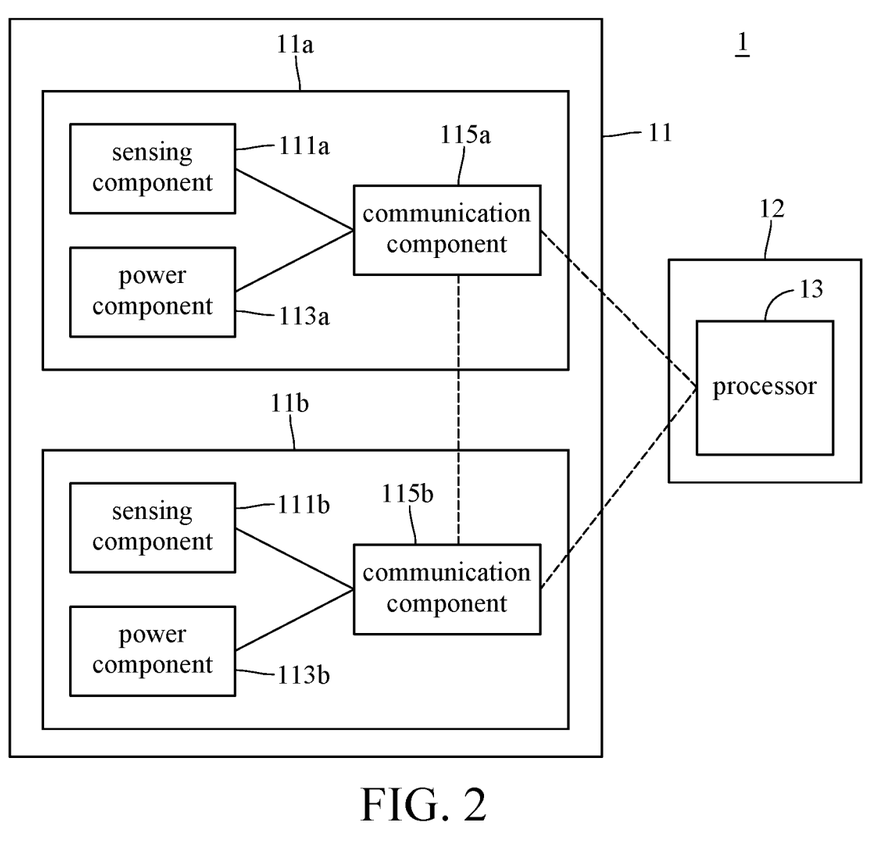
FIG. 2 is a detailed functional block diagram of a joint bending state determining device according to an embodiment of this invention.

Please refer to FIG. 2 that is a detailed functional block diagram of the joint bending state determining device 1 according to an embodiment of this invention. FIG. 2 exemplarily illustrates the components included in the first and second gravity sensors 11a and 11b of the joint bending state determining device 1, and the connections between the processor and the first and second gravity sensors 11a and 11b. As shown in FIG. 2, the first gravity sensor 111a can comprise a sensing component 111a, a power component 113a and a communication component 115a; the second gravity sensor 11b can comprise a sensing component 111b, a power component 113b and a communication component 115b.

Each of the sensing components 111a and 111b can comprise a triaxial accelerometer. The sensing component 111a is configured to perform gravity sensing to generate the aforementioned first polar angle and first azimuth angle, and the sensing component 111b is configured to perform gravity sensing to generate the aforementioned second polar angle and second azimuth angle. In another embodiment, each of the sensing components 111a and 111b further comprises a gyroscope. The power components 113a and 113b are configured to supply the electric power to the electronic components included in the first and second gravity sensors 11a and 11b respectively. For example, the power components 113a and 113b are batteries, but their specifications are not limited in this invention. The communication components 115a and 115b can be chip components supporting Bluetooth, Wi-Fi, near-field communication (NFC) and other short-range communication standards. The communication components 115a and 115b can establish communication connections with the processor 13 respectively, and can also establish a communication connection with each other.

FIG. 2 exemplarily illustrates that any two of the processor 13, the communication component 115a of the first gravity sensor 11a and the communication component 115b of the second gravity sensor 11b have a communication connection with each other. In another embodiment, the processor 13 can merely have a communication connection with one of the first and second gravity sensors 11a and 11b. In yet another embodiment, the first and second gravity sensors 11a and 11b can have no communication connection with each other but each have a communication connection with the processor 13. In other embodiments, in addition to the components shown in FIG. 2, one or two of the first and second gravity sensors 11a and 11b can each include a processing component, such as a central processing unit, a microcontroller, a programmable logic controller, etc. The processing component is configured to perform the preliminary calculation and determining procedure on the information generated by the sensing component of the gravity sensor where the processing component is disposed, or on the information which is obtained through the communication component and generated by the other gravity sensor.

Figure 3:
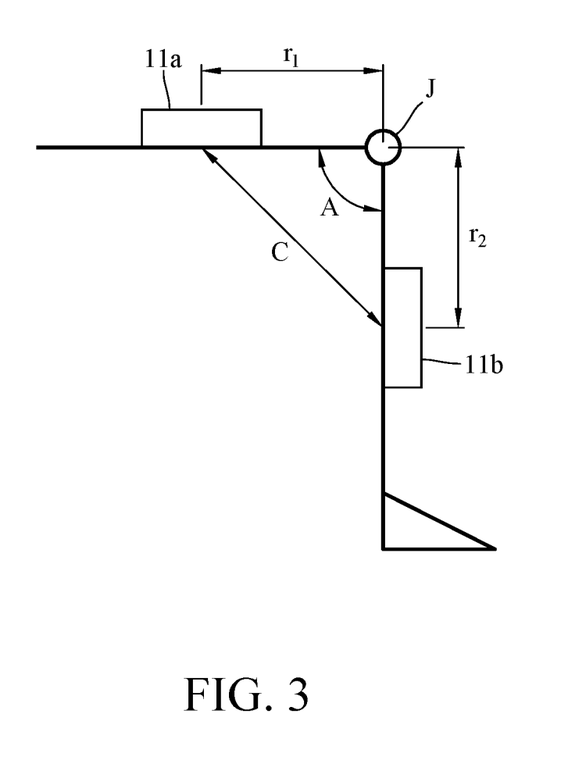
FIG. 3 is a schematic diagram of the placement of first and second gravity sensors of a joint bending state determining device according to an embodiment of this invention.

Please refer to FIG. 1 and FIG. 3, wherein FIG. 3 is a schematic diagram of the placement of the first and second gravity sensors 11a and 11b according to an embodiment of this invention. As aforementioned, the first and second gravity sensors 11a and 11b can be disposed on limbs of a human body connected by a joint such as a knee, an elbow, a hip joint, etc. The processor 13 can determine the bending state of the joint according to the information corresponding to the locations of the first and second gravity sensors 11a and 11b. The following embodiment takes the knee as an example. As shown in FIG. 3, the first gravity sensor 11a is disposed on the upper leg of the user and has a distance of first length $r_1$ from the joint J (knee); the second gravity sensor 11b is disposed on the lower leg of the user and has a distance of second length $r_2$ from the joint J. The first length $r_1$ and the second length $r_2$ can be any lengths that are equal or unequal, and are not limited in this invention. In particular, a tolerance difference between the first length $r_1$ and the distance between the actual location of the first gravity sensor 11a and the knee is acceptable, such as 3-5 cm, and the same is true for the second length $r_2$. Moreover, the tolerance difference can be determined based on the joint angle. In terms of measuring the knee angle of 60 degrees, within the error of plus or minus 5 degrees (55-65 degrees), the tolerance difference (the error of the distance between the location of the first gravity sensor 11a and the knee) is plus or minus 1.2 cm; in terms of measuring the knee angle of 90 degrees, within the error of plus or minus 5 degrees (85-95 degrees), the tolerance difference is plus or minus 1.8 cm. FIG. 3 exemplarily illustrates that the first and second gravity sensors 11a and 11b are disposed on the front sides of the upper leg and the lower leg respectively. In another embodiment, the first and second gravity sensors 11a and 11b can disposed on the outer sides of the upper leg and the lower leg respectively.

As aforementioned, the first gravity sensor 11a can generate the first polar angle and the first azimuth angle, and the second gravity sensor 11b can generate the second polar angle and the second azimuth angle. More particularly, the first polar angle indicates the included angle between the extension direction of the first length $r_1$ and a first Z axis parallel to the gravity axis to the ground; the first azimuth angle indicates the included angle between a first projection and a second projection, wherein the first projection indicates the projection of the extension direction of the first length $r_1$ on a first X-Y plane (parallel to the horizontal plane) whose normal vector is the first Z axis, and the second projection indicates the projection of a first X axis parallel to the axis towards the Magnetic North on the first X-Y plane; the second polar angle indicates the included angle between the extension direction of the second length $r_2$ and a second Z axis parallel to the gravity axis to the ground; and the second azimuth angle indicates the included angle between a third projection and a fourth projection, wherein the third projection indicates the projection of the extension direction of the second length $r_2$ on a second X-Y plane (parallel to the horizontal plane) whose normal vector is the second Z axis, and the fourth projection indicates the projection of a second X axis parallel to the axis towards the Magnetic North on the second X-Y plane.

The processor 13 can obtain the first length $r_1$ corresponding to the first gravity sensor 11a and the second length $r_2$ corresponding to the second gravity sensor 11b through the aforementioned input interface. For example, the user can dispose the first gravity sensor 11a anywhere on the upper leg and dispose the second gravity sensor 11b anywhere on the lower leg according to the needs, and then roughly measure the distance between the knee and the location where the first gravity sensor 11a is disposed (e.g. the location of the center of the first gravity sensor 11a) and input this distance into the input interface as the first length $r_1$, and roughly measure the distance between the knee and the location where the second gravity sensor 11b is disposed (e.g. the location of the center of the second gravity sensor 11b) and input this distance into the input interface as the second length $r_2$. For example, the first and second gravity sensors 11a and 11b can each be equipped with a tape measure, wherein the outlet end of the tape measure is set to be at the center of the first gravity sensor 11a or the second gravity sensors 11b. Accordingly, the user can pull out the tap measures from the first and second gravity sensors 11a and 11b to measure the first length $r_1$ and the second length $r_2$ respectively, but this invention is not limited to this.

The processor 13 also obtains the first polar angle and the first azimuth angle generated by the first gravity sensor 11a and the second polar angle and the second azimuth angle generated by the second gravity sensor 11b from the sensor group 11. The steps of obtaining the above-mentioned first length $r_1$, second length $r_2$, first polar angle, first azimuth angle, second polar angle and second azimuth angle can be collectively referred to as an information obtaining procedure. After the information obtaining procedure, the processor 13 can then perform a joint bending state determining procedure. In an embodiment, in the information obtaining procedure, the steps of obtaining the first and second length $r_1$ and $r_2$ can precede the steps of obtaining the first polar angle, the first azimuth angle, the second polar angle and the second azimuth angle. More particularly, after obtaining the first length $r_1$ and the second length $r_2$ from the input interface, the processor 13 can be triggered to ask the sensor group 11 for the first polar angle, the first azimuth angle, the second polar angle and the second azimuth angle. In another embodiment, the processor 13 stores the first length $r_1$ and the second length $r_2$ in a memory or a cloud database, and periodically obtains the first length $r_1$, the second length $r_2$, the first polar angle, the first azimuth angle, the second polar angle and the second azimuth angle to perform the joint bending state determining procedure. In this embodiment, the order of obtaining the above information is not limited.

The above-mentioned joint bending state determining procedure can comprise: obtaining a set of coordinates of the joint J in a coordinate system according to the first polar angle, the first azimuth angle and the first length $r_1$; obtaining a set of coordinates of the second gravity sensor 11b in the coordinate system according to the set of coordinates of the joint J, the second polar angle, the second azimuth angle and the second length $r_2$; and obtaining the angle of the joint J (joint angle A) according to the set of coordinates of the second gravity sensor 11b in the coordinate system, the first length $r_1$ and the second length $r_2$. More particularly, by the above procedure, the processor 13 can transform the coordinate system of the second gravity sensor 11b into the same coordinate system as the first gravity sensor 11a, so as to obtain the distance C between the first gravity sensor 11a and the second gravity sensor 11b, and then obtain the joint angle A according to the distance C, the first length $r_1$, the second length $r_2$ and the cosine rule.

Figure 4A:
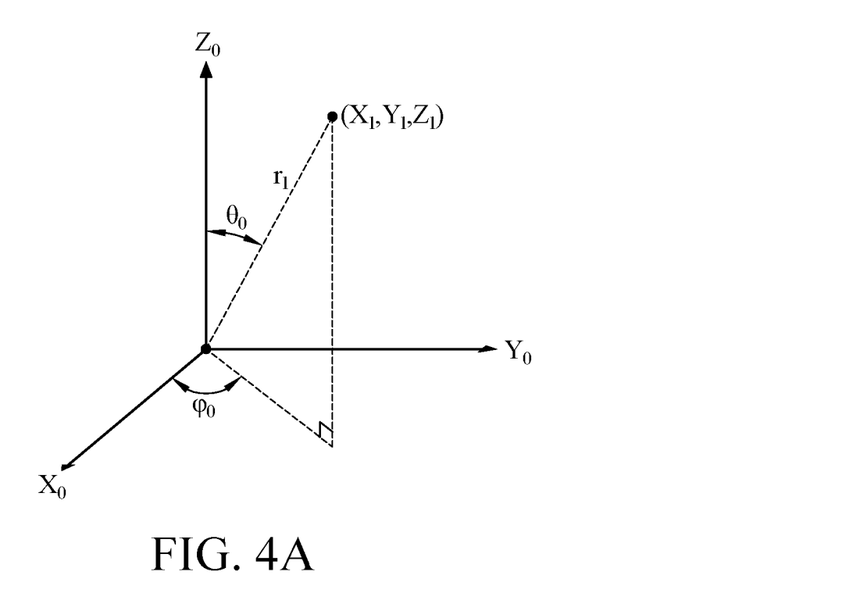
FIG. 4A and FIG. 4B exemplarily illustrate the transformation of the coordinate system in a joint bending state determining procedure of a joint bending state determining device according to an embodiment of this invention.
Figure 4B:
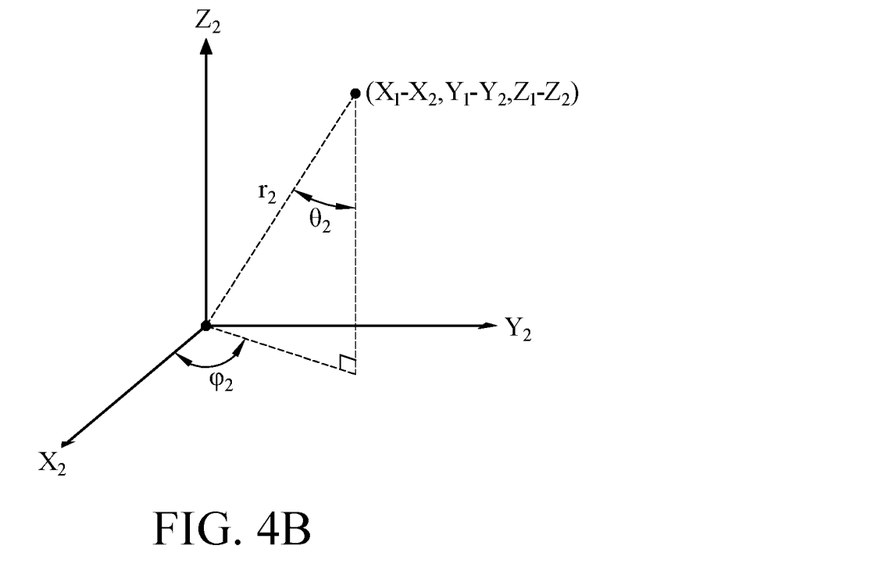

Please refer to FIG. 1, FIG. 3, FIG. 4A and FIG. 4B for the further explanation of the determining procedure performed by the processor 13 as describe above, wherein FIG. 4A and FIG. 4B exemplarily illustrate the transformation of the coordinate system in the joint bending state determining procedure. As shown in FIG. 4A, the processor 13 can the set of coordinates $(X_1, Y_1, Z_1)$ of the joint J in a coordinate system according to the first polar angle $\theta_0$ and the first azimuth angle $\varphi_0$ generated by the first gravity sensor 11a and the first length $r_1$, wherein the set of coordinates $(X_0, Y_0, Z_0)$ of the first gravity sensor 11a serves as the origin of the coordinate system. The axis $Z_0$ shown in FIG. 4A, as the aforementioned first Z axis, indicates the direction parallel to the gravity axis to the ground. The plane $X_0$-$Y_0$ shown in FIG. 4A, as the aforementioned first X-Y plane, indicates the plane perpendicular to the gravity axis to the ground. As aforementioned, the first polar angle $\theta_0$ indicates the included angle between the extension direction of the upper leg (i.e. the extension direction of the first length $r_1$) and the gravity axis, and the first azimuth angle $\varphi_0$ indicates the included angle between the projection of the extension direction of the first length $r_1$ on the horizontal plane and the projection of the axis towards the Magnetic North on the horizontal plane. More particularly, the processor 13 can obtain a first x coordinate $X_1$ according to the first length $r_1$, the sine value of the first polar angle $\theta_0$, and the cosine value of the first azimuth angle $\varphi_0$, obtain a first y coordinate $Y_1$ according to the first length $r_1$, the sine value of the first polar angle $\theta_0$ and the sine value of the first azimuth angle $\varphi_0$, and obtain a first z coordinate $Z_1$ according to the first length $r_1$ and the cosine value of first polar angle $\theta_0$, and group the first x coordinate $X_1$, the first y coordinate $Y_1$ and the first z coordinate $Z_1$ together to form the set of coordinates $(X_1, Y_1, Z_1)$ of the joint J. More specifically, the processor 13 can perform calculations of the following equations to obtain the set of coordinates $(X_1, Y_1, Z_1)$ of the joint J.

$$X_1 = r_1 \times \sin(\theta_0) \times \cos(\varphi_0)$$

$$Y_1 = X_1 \times \tan(\varphi_0) = r_1 \times \sin(\theta_0) \times \sin(\varphi_0)$$

$$Z_1 = r_1 \times \cos(\theta_0)$$

Then, the processor 13 can obtain the set of coordinates $(X_2, Y_2, Z_2)$ of the second gravity sensor 11b in the coordinate system according to the set of coordinates $(X_1, Y_1, Z_1)$ of the joint J, the second length $r_2$ and the second polar angle $\theta_2$ and the second azimuth angle $\varphi_2$ generated by the second gravity sensor 11b, wherein the set of coordinates $(X_0, Y_0, Z_0)$ of the first gravity sensor 11a serves as the origin of the coordinate system. More particularly, the processor 13 assumes that the set of coordinates of the second gravity sensor 11b in the coordinate system, whose origin is the set of coordinates $(X_0, Y_0, Z_0)$ of the first gravity sensor 11a, is $(X_2, Y_2, Z_2)$, so that in this coordinate system, the set of coordinates of the joint J can be regarded as being translated into $(X_1-X_2, Y_1-Y_2, Z_1-Z_2)$ as shown in FIG. 4B. In FIG. 4B, the axis $Z_2$, as the aforementioned second Z axis, indicates the direction parallel to the gravity axis to the ground, and the plane $X_2$-$Y_2$, as the aforementioned second X-Y plane, indicates the plane perpendicular to the gravity axis to the ground. The second polar angle $\theta_2$ indicates the included angle between the extension direction of the lower leg (i.e. the extension direction of the second length $r_2$) and the gravity axis, and the second azimuth angle $\varphi_2$ indicates the included angle between the projection of the extension direction of the second length $r_2$ on the horizontal plane and the projection of the axis towards the Magnetic North on the horizontal plane. The processor 13 can obtain a second x coordinate $X_2$ according to the first x coordinate $X_1$ obtained in FIG. 4A, the second length $r_2$, the sine value of the second polar angle $\theta_2$ and the cosine value of the second azimuth angle $\varphi_2$, obtain a second y coordinate $Y_2$ according to the first y coordinate $Y_1$, the first x coordinate $X_1$, second x coordinate $X_2$ and the tangent value of the second azimuth angle $\varphi_2$, and obtain a second z coordinate $Z_2$ according to the first z coordinate $Z_1$, the second length $r_2$ and the cosine value of the second polar angle $\theta_2$, and then group the second x coordinate $X_2$, the second y coordinate $Y_2$ and the second z coordinate $Z_2$ together to form the set of coordinates $(X_2, Y_2, Z_2)$ of the second gravity sensor 11b in the coordinate system whose origin is the set of coordinates $(X_0, Y_0, Z_0)$ of the first gravity sensor 11a. More specifically, the processor 13 can perform calculations of the following equations to obtain the set of coordinates $(X_2, Y_2, Z_2)$ of the second gravity sensor 11b.

$$X_1 - X_2 = r_2 \times \sin(\theta_2) \times \cos(\varphi_2) \Rightarrow X_2 = X_1 - r_2 \times \sin(\theta_2) \times \cos(\varphi_2)$$

$$Y_1 - Y_2 = (X_1 - X_2) \times \tan(\varphi_2) \Rightarrow Y_2 = Y_1 - (X_1 - X_2) \times \tan(\varphi_2)$$

$$Z_1 - Z_2 = r_2 \times \cos(\theta_2) \Rightarrow Z_2 = Z_1 - r_2 \times \cos(\theta_2)$$

Through the above calculation, the processor 13 can obtain the set of coordinates $(X_2, Y_2, Z_2)$ of the second gravity sensor 11b in the coordinate system whose origin is the set of coordinates $(X_0, Y_0, Z_0)$ of the first gravity sensor 11a, and the processor 13 can calculate the distance C between the first gravity sensor 11a and the second gravity sensor 11b by the following equation.

$$C^2 = (X_2 - X_0)_2 + (Y_2 - Y_0)^2 + (Z_2 + Z_0)^2$$

Then, the processor 13 obtains the joint angle A according to the cosine rule as shown below.

$$-\cos(A) = \frac{C^2 - r_1^2 - r_2^2}{2 \times r_1 \times r_2}$$

The processor 13 can output the calculated joint angle A through the output interface and/or record the calculated joint angle A in a memory or a cloud database. In the above description, the first gravity sensor 11a is exemplarily described to be disposed on the upper leg, and the second gravity sensor 11b is exemplarily described to be disposed on the lower leg. In other embodiments, the first gravity sensor 11a can be disposed on the lower leg and the second gravity sensor 11b can be disposed on the upper leg. By the above-mentioned calculations, each of the two gravity sensors of the joint bending state determining device 1 does not need to be limited to a specific one of the upper and lower legs when they are worn; that is, the positions of the two gravity sensors can be swapped up and down. Accordingly, the convenience of use may be improved.

Figure 5A:
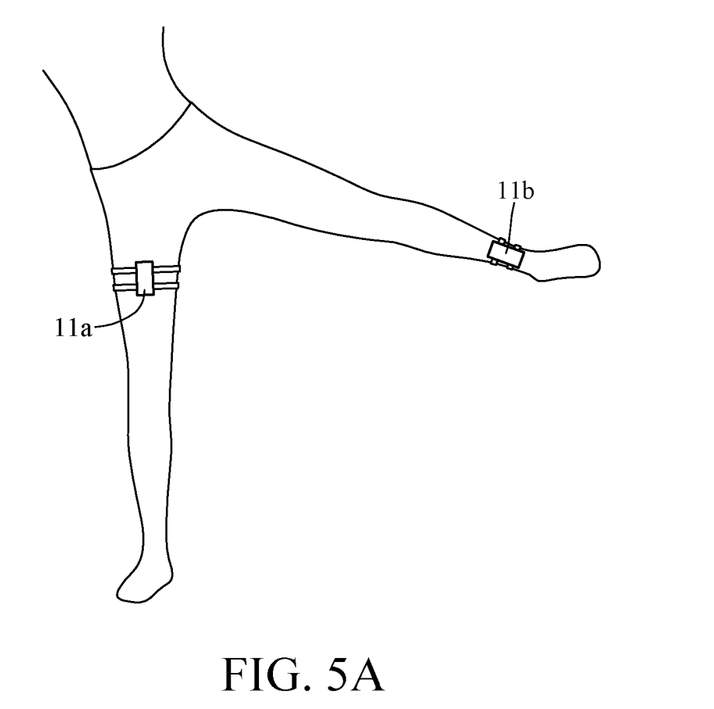
FIG. 5A is a schematic diagram of the placement of first and second gravity sensors of a joint bending state determining device according to another embodiment of this invention.
Figure 5B:
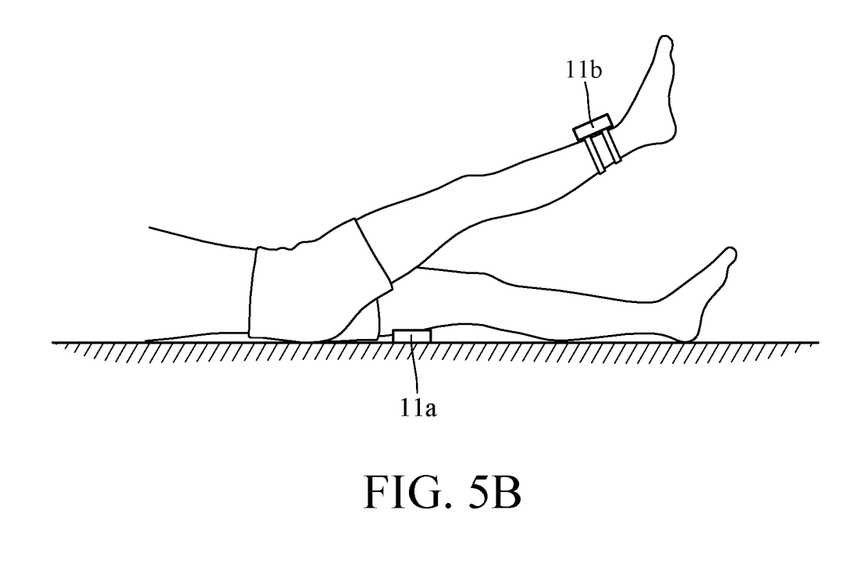
FIG. 5B is a schematic diagram of the placement of first and second gravity sensors of a joint bending state determining device according to yet another embodiment of this invention.

The above embodiment exemplarily describes that the first and second gravity sensors 11a and 11b are disposed on the upper and lower legs, and the processor 13 can determine the bending state of the knee according to the information corresponding to the locations of the first and second gravity sensors 11a and 11b. The principles for determining the bending state of the joint as described above can also be applied to determining the bending state of a hip joint. Please refer to FIG. 5A and FIG. 5B, wherein FIG. 5A and FIG. 5B exemplarily illustrate the placement of the first and second gravity sensors 11a and 11b as the joint bending state determining device 1 is applied to determining the bending state of a hip joint. As shown in FIG. 5A, the first and second gravity sensors 11a and 11b can be respectively disposed at the upper leg of one lower limb of the user and the lower leg of the other lower limb of the user. As shown in FIG. 5B, when the user is lying on a flat surface, the first and second gravity sensors 11a and 11b can be respectively disposed on this flat surface and the lower leg of one lower limb of the user. In particular, the lower limb whose lower leg is equipped with a gravity sensor is the affected limb. Moreover, the first and second gravity sensors 11a and 11b shown in both of FIG. 5A and FIG. 5B can be swapped with each other. In the embodiments of FIG. 5A and FIG. 5B, the processor 13 can perform the information obtaining procedure and the joint bending state determining procedure as described in the preceding embodiment, so as to obtain the joint angle of the hip joint.

As aforementioned, before the processor 13 performs the step of obtaining the joint angle in the joint bending state determining procedure, the processor 13 obtains the first length $r_1$ corresponding to the first gravity sensor 11a and the second length $r_2$ corresponding to the second gravity sensor 11b through the input interface. In an embodiment, each of the assistive devices where the first gravity sensor 11a and the second gravity sensor 11b are respectively disposed comprises an input interface. Therefore, the processor 13 can consider the input value obtained from the input interface corresponding to the first gravity sensor 11a to be the first length $r_1$, and consider the input value obtained from the input interface corresponding to the second gravity sensor 11b to be the second length $r_2$.

In the embodiment in which the joint bending state determining device 1 merely comprises one input interface, before the step of obtaining the set of coordinates of the joint, the joint bending state determining device 1 can perform a sensor recognition sub-procedure so as to determine the correspondence between the two gravity sensors of the joint bending state determining device 1 and the input length values. In other words, the joint bending state determining procedure can further comprise the sensor recognition sub-procedure before the step of obtaining the set of coordinates of the joint.

Figure 6:
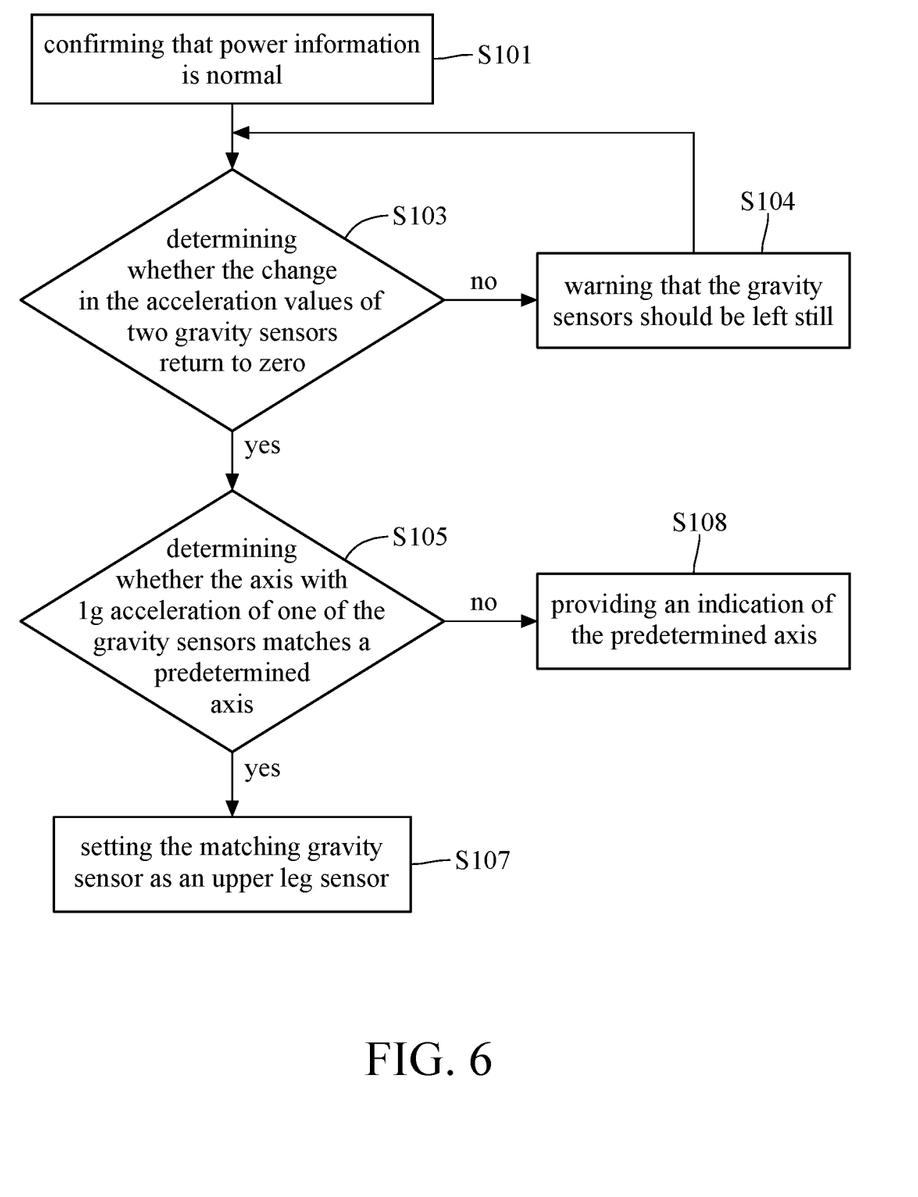
FIG. 6 is a flow chart of a sensor recognition sub-procedure of a joint bending state determining device according to an embodiment of this invention.

Please refer to FIG. 1, FIG. 3 and FIG. 6, wherein FIG. 6 is a flow chart of a sensor recognition sub-procedure of the joint bending state determining device 1 according to an embodiment of this invention. The setting implementation of FIG. 3 is used to exemplify the sensor recognition sub-procedure shown in FIG. 6. Through the input interface, the user inputs the distance between the joint J and the gravity sensor disposed at the upper leg as the first length $r_1$, and inputs the distance between the joint J and the gravity sensor disposed at the lower leg as the second length $r_2$. In step S101, the processor 13 of the joint bending state determining device 1 can acquire the power information of the two gravity sensor and confirm it is normal. In step S103, the processor 13 detects the acceleration values of the two gravity sensors and determines whether the change in the acceleration values of the two gravity sensors return to zero. More particularly, step S103 can determine whether the user moves his/her limb equipped with the gravity sensor. If the determined result of step S103 is no, the processor 13 performs step S104 to generate a warning signal to warn the user to keep the setting positions of the gravity sensors still, and then performs step S103 again. If the determined result of step S103 is yes, the processor 13 performs step S105 to determine whether the axis with 1 g acceleration of one of the gravity sensors matches a predetermined axis. If the determined result of step S105 is yes, the processor 13 performs step S107 to set the matching gravity sensor as the gravity sensor located above the knee (hereinafter called "upper leg sensor").

More particularly, said axis with 1 g acceleration indicates the gravity axis to the ground. In the embodiment shown in FIG. 3, the predetermined axis can be set as the predetermined z-axis of the gravity sensor, which means that the processor 13 will set the gravity sensor which is horizontal at the gravity axis to the ground as the upper leg sensor (the first gravity sensor 11a in FIG. 3). In other words, the processor 13 can determine whether the predetermined z-axis of any gravity sensor matches the gravity axis to the ground, and set the matching one as the upper leg sensor. Therefore, the processor 13 can determine that the first length $r_1$ corresponds to the first gravity sensor 11a. If the determined result of step S103 is no, which means no gravity sensor's axis with 1 g acceleration matches the predetermined axis or both gravity sensors' axes with 1 g acceleration match the predetermined axis, the processor 13 performs step S108 to generate an indication of the predetermined axis for reminding the user to keep the upper leg horizontal and the lower leg not horizontal. The above-mentioned setting implementation of the gravity sensors and the setting content of the predetermined axis are merely examples, and this invention is not limited thereto. Moreover, the above-mentioned steps S101, S103, S104 and S108 are optional steps. In an embodiment, the processor 13 can merely perform steps S105 and S107, and in this embodiment, when the determined result of step S105 is no, the processor 13 can output an indication of recognition error.

The sensor recognition sub-procedure as described above is performed by the processor 13, but in another embodiment, the sensor recognition sub-procedure can be performed by the first gravity sensor 11a or the second gravity sensor 11b. As aforementioned, the first gravity sensor 11a can comprise a processing component, and the second gravity sensor 11b can also comprise a processing component. The sensor recognition sub-procedure can be performed by the processing component of the first gravity sensor 11a or the second gravity sensor 11b, wherein the content of the sensor recognition sub-procedure is substantially the same as that performed by the processor 13 except for the difference that the first gravity sensor 11a or the second gravity sensor 11b will notify the processor 13 of the determined gravity sensor so as to allow the processor 13 to determine that the obtained first length $r_1$ and second length $r_2$ respectively correspond to the first gravity sensor 11a and second gravity sensor 11b.

Moreover, during the information obtaining procedure before the joint bending state determining procedure, the joint bending state determining device 1 can perform a charge level determining sub-procedure on the first and second gravity sensors 11a and 11b; that is, the aforementioned information obtaining procedure can comprise the charge level determining sub-procedure. The charge level determining sub-procedure comprises comparing the charge level (first charge level) of the power component (the power component 113a in FIG. 2) of the first gravity sensor 11a with the charge level (second charge level) of the power component (the power component 113b in FIG. 2) of the second gravity sensor 11b, so as to determine which one of the first and second gravity sensors 11a and 11b to collect the information (such as the aforementioned polar angle, azimuth angle) generated by itself and the other party and to transmit the collected information to the processor 13 for the joint bending state determining procedure.

In an embodiment, the charge level determining sub-procedure can be performed by the processor 13. The processor 13 can obtain the first charge level and the second charge level. The processor 13 controls the first gravity sensor 11a to capture the second polar angle and the second azimuth angle from the second gravity sensor 11b, and to return the second polar angle, the second azimuth angle, and the first polar angle and the first azimuth angle which the first gravity sensor 11a senses to the processor 13 in response to determining that the first charge level is higher than the second charge level; in contrast, the processor 13 controls the second gravity sensor 11b to capture the first polar angle and the first azimuth angle from the first gravity sensor 11a, and to return the first polar angle, the first azimuth angle, and the second polar angle and the second azimuth angle which the second gravity sensor 11b senses to the processor 13 in response to determining that the first charge level is lower than the second charge level.

In another embodiment, the charge level determining sub-procedure can be performed by the first gravity sensor 11a or the second gravity sensor 11b. As aforementioned, the first gravity sensor 11a can comprise a processing component, and the second gravity sensor 11b can also comprise a processing component. The charge level determining sub-procedure can be performed by the processing component of one of the first and second gravity sensors 11a and 11b. For the implementation of the first gravity sensor 11a, the first gravity sensor 11a can obtain the second charge level from the second gravity sensor 11b. The first gravity sensor 11a captures the second polar angle and the second azimuth angle from the second gravity sensor 11b, and transmits the second polar angle, the second azimuth angle, and the first polar angle and the first azimuth angle which the first gravity sensor 11a senses to the processor 13 in response to determining that the first charge level is higher than the second charge level; in contrast, the first gravity sensor 11a transmits the first polar angle and the first azimuth angle to the second gravity sensor 11b in response to determining that the first charge level is lower than the second charge level, and the second gravity sensor 11b transmits the first polar angle, the first azimuth angle, the second polar angle and the second azimuth angle to the processor 13.

For the implementation of the second gravity sensor 11b, the second gravity sensor 11b can obtain the first charge level from the first gravity sensor 11a. The second gravity sensor 11b captures the first polar angle and the first azimuth angle from the first gravity sensor 11a, and transmits the first polar angle, the first azimuth angle, and the second polar angle and the second azimuth angle which the second gravity sensor 11b senses to the processor 13 in response to determining that the second charge level is higher than the first charge level; in contrast, the second gravity sensor 11b transmits the second polar angle and the second azimuth angle to the first gravity sensor 11a in response to determining that the second charge level is lower than the first charge level, and the first gravity sensor 11a transmits the first polar angle, the first azimuth angle, the second polar angle and the second azimuth angle to the processor 13. In short, the first gravity sensor 11a or the second gravity sensor 11b will capture the polar angle and the azimuth angle of the other party in response to determining that its charge level is higher than the charge level of the other party, and will provide its polar angle and azimuth angle to the other party in response to determining that its charge level is lower than the charge level of the other party.

In yet another embodiment, the first and second gravity sensors 11a and 11b both perform the charge level determining sub-procedure. In this embodiment, the first and second gravity sensors 11a and 11b can capture the charge levels from each other by issuing a capture request, or provide their own charge levels by broadcasting. When the gravity sensor determines that its charge level is higher than that of the other gravity sensor, and receives the polar angle and the azimuth angle sensed by the other gravity sensor, the gravity sensor can confirm that its judgment is correct, thereby double checking.

By the above charge level determining sub-procedure, the joint bending state determining device can first determine the gravity sensor with a higher charge level to be the main transmission hardware. The joint bending state determining device can set the main transmission hardware component to collect the information sensed by the two hardware components (gravity sensors) when performing the information obtaining procedure before the joint bending state determining procedure and to transmit the collected information to the processor of the user device. Accordingly, the problem that the information transmission time of the two gravity sensors is not synchronized may be avoided. Moreover, since the distance between the two gravity sensors is less than the distance between any one of the two gravity sensors and the user device, the above-mentioned setting of the main transmission hardware may save the power consumed by the gravity sensor with a lower charge level. Further, the power usage effectiveness may be improved.

The charge level determining sub-procedure in each of the aforementioned embodiments can further comprise the step of confirming whether the power information is normal. More particularly, the processor 13/first gravity sensor 11a/second gravity sensor 11b can determine whether the first/second charge level is higher than a predetermined operating charge level, wherein the predetermined operating charge level can indicate the minimum power required for the first gravity sensor 11a/second gravity sensor 11b to work. If the determined result is yes, the power information is confirmed as normal; if the determined result is no, the power information is abnormal and the corresponding warning signal is generated. In an example, the processor 13 can output the warning signal through the output interface. In another example, the first gravity sensor 11a/second gravity sensor 11b can have a warning component such as a warning light, a speaker, etc., and the warning component can output the warning signal as a light or sound.

This invention also provides a joint bending state determining method that can comprise the information obtaining procedure described in any one of the preceding embodiments and the joint bending state determining procedure described in any one of the preceding embodiments. In an embodiment, the joint bending state determining method can be one or more instructions/application programs (APP) stored in a non-transitory computer-readable medium, such as a read-only memory, a hard disk, etc. in the user device, or a hard disk included in a cloud server. For example, the user can download an application program of the joint bending state determining method from the cloud server by the user device, and use the processor of the user device to run this application program.

In view of the above description, the joint bending state determining device and method provided in this invention can perform the procedure for determining the bending state of a joint by merely two sensors. Therefore, the difficulty of charging, storage and wearing of the joint bending state determining device may be reduced, and the device may be lighter. For the joint bending state determining device provided in this invention, the distances respectively between the two sensors and the joint is not limited. Accordingly, the user may freely choose the suitable assistive device or protective gear to dispose the two sensors according to the needs. The joint bending state determining device provided in this invention does not need to be equipped with an exclusive assistive device or protective gear. In addition, the joint bending state determining device may improve the freedom of wearing without restricting the wearing positions of the two sensors. Moreover, the joint bending state determining device provided in this invention can specify the main transmission hardware component based on the charge levels of the hardware components, so that the problem that the information transmission times of the two sensors are asynchronous may be avoided, and the power usage effectiveness may be improved.

What is claimed is:

1. A joint bending state determining device, comprising:
   a sensor group comprising:
      a first gravity sensor configured to generate a first polar angle and a first azimuth angle; and
      a second gravity sensor configured to generate a second polar angle and a second azimuth angle; and
   a processor connected with the sensor group, and configured to obtain a first length corresponding to the first gravity sensor and a second length corresponding to the second gravity sensor, to obtain a set of coordinates of a joint in a coordinate system according to the first polar angle, the first azimuth angle and the first length, to obtain a set of coordinates of the second gravity sensor in the coordinate system according to the set of coordinates of the joint, the second polar angle, the second azimuth angle and the second length, and to obtain a joint angle according to the set of coordinates of the second gravity sensor in the coordinate system, the first length and the second length;
   wherein the first length is associated with a distance between the first gravity sensor and the set of coordinates of the joint, and the second length is associated with a distance between the second gravity sensor and the set of coordinates of the joint; and
   wherein the processor is further configured to obtain a first charge level of the first gravity sensor and a second charge level of the second gravity sensor, to control the first gravity sensor to capture the second polar angle and the second azimuth angle from the second gravity sensor and return the second polar angle and the second azimuth angle to the processor in response to determining that the first charge level is higher than the second charge level, and to control the second gravity sensor to capture the first polar angle and the first azimuth angle from the first gravity sensor and return the first polar angle and the first azimuth angle to the processor in response to determining that the first charge level is lower than the second charge level; or
   wherein the first gravity sensor has the first charge level and is further configured to obtain the second charge level of the second gravity sensor, to capture the second polar angle and the second azimuth angle from the second gravity sensor and transmit the second polar angle and the second azimuth angle to the processor in response to determining that the first charge level is higher than the second charge level, and to transmit the first polar angle and the first azimuth angle to the second gravity sensor in response to determining that the first charge level is lower than the second charge level.

2. The joint bending state determining device according to claim 1, wherein the processor obtains the set of coordinates of the joint by obtaining a first x coordinate according to the first length, a sine value of the first polar angle and a cosine value of the first azimuth angle, obtaining a first y coordinate according to the first length, the sine value of the first polar angle and a sine value of the first azimuth angle, obtaining a first z coordinate according to the first length and a cosine value of the first polar angle, and grouping the first x coordinate, the first y coordinate and the first z coordinate to form the set of coordinates of the joint.

3. The joint bending state determining device according to claim 2, wherein the processor obtains the set of coordinates of the second gravity sensor in the coordinate system by obtaining a second x coordinate according to the first x coordinate, the second length, a sine value of the second polar angle and a cosine value of the second azimuth angle, obtaining a second y coordinate according to the first y coordinate, the first x coordinate, the second x coordinate and a tangent value of the second azimuth angle, obtaining a second z coordinate according to the first z coordinate, the second length and a cosine value of the second polar angle, and grouping the second x coordinate, the second y coordinate and the second z coordinate to form the set of coordinates of the second gravity sensor in the coordinate system.

4. The joint bending state determining device according to claim 1, wherein the processor obtains the joint angle by obtaining a distance between an origin and the set of coordinates of the second gravity sensor in the coordinate system, and obtaining the joint angle according to the distance between the origin and the set of coordinates of the second gravity sensor in the coordinate system, the first length, the second length and a cosine rule.

5. The joint bending state determining device according to claim 1, wherein before obtaining the set of coordinates of the joint, the processor is further configured to determine that a predetermined axis of the first gravity sensor matches a gravity axis to ground and accordingly determine that the first gravity sensor corresponds to the first length.

6. The joint bending state determining device according to claim 1, wherein before the processor obtains the set of coordinates of the joint, the first gravity sensor is further configured to determine that a predetermined axis of the first gravity sensor matches a gravity axis to ground and notify the processor to allow the processor to determine that first gravity sensor corresponds to the first length.

7. The joint bending state determining device according to claim 1, wherein the processor is disposed on a same circuit board as the first gravity sensor or the second gravity sensor.

8. The joint bending state determining device according to claim 1, further comprising an input interface that is connected with the processor and configured to receive the first length and the second length.

9. A joint bending state determining method, comprising:
   obtaining a first length corresponding to a first gravity sensor and a second length corresponding to a second gravity sensor;
   using one of the first gravity sensor and the second gravity sensor which has a higher charge level to collect information of a first polar angle and a first azimuth angle generated by the first gravity sensor and a second polar angle and a second azimuth angle generated by the second gravity sensor and to transmit the information to a processor;

obtaining a set of coordinates of a joint in a coordinate system according to the first polar angle, the first azimuth angle and the first length;

obtaining a set of coordinates of the second gravity sensor in the coordinate system according to the set of coordinates of the joint, the second polar angle, the second azimuth angle and the second length; and obtaining a joint angle according to the set of coordinates of the second gravity sensor in the coordinate system, the first length and the second length;

wherein the first length is associated with a distance between the first gravity sensor and the set of coordinates of the joint, and the second length is associated with a distance between the second gravity sensor and the set of coordinates of the joint; and wherein using the one of the first gravity sensor and the second gravity sensor which has the higher charge level to collect the information of the first polar angle and the first azimuth angle generated by the first gravity sensor and the second polar angle and the second azimuth angle generated by the second gravity sensor and to transmit the information to the processor comprises:

obtaining a first charge level of the first gravity sensor and a second charge level of the second gravity sensor;

controlling the first gravity sensor to capture the second polar angle and the second azimuth angle from the second gravity sensor and return the second polar angle and the second azimuth angle in response to the first charge level being higher than the second charge level to the processor; and controlling the second gravity sensor to capture the first polar angle and the first azimuth angle from the first gravity sensor and return the first polar angle and the first azimuth angle in response to the first charge level being lower than the second charge level to the processor; or wherein the first gravity sensor has the first charge level, and using the one of the first gravity sensor and the second gravity sensor which has the higher charge level to collect the information of the first polar angle and the first azimuth angle generated by the first gravity sensor and the second polar angle and the second azimuth angle generated by the second gravity sensor and to transmit the information to the processor comprises:

by the first gravity sensor, obtaining the second charge level of the second gravity sensor;

capturing the second polar angle and the second azimuth angle from the second gravity sensor and transmitting the second polar angle and the second azimuth angle by the first gravity sensor to the processor in response to the first charge level being higher than the second charge level; and transmitting the first polar angle and the first azimuth angle to the second gravity sensor to the processor by the first gravity sensor, and transmitting the first polar angle, the first azimuth angle, the second polar angle and the second azimuth angle by the second gravity sensor in response to the first charge level being lower than the second charge level.

10. The joint bending state determining method according to claim 9, wherein obtaining the set of coordinates of the joint in the coordinate system according to the first polar angle, the first azimuth angle and the first length comprises:

obtaining a first x coordinate according to the first length, a sine value of the first polar angle and a cosine value of the first azimuth angle;

obtaining a first y coordinate according to the first length, the sine value of the first polar angle and a sine value of the first azimuth angle;

obtaining a first z coordinate according to the first length and a cosine value of the first polar angle; and grouping the first x coordinate, the first y coordinate and the first z coordinate to form the set of coordinates of the joint.

11. The joint bending state determining method according to claim 10, wherein obtaining the set of coordinates of the second gravity sensor in the coordinate system according to the set of coordinates of the joint, the second polar angle, the second azimuth angle and the second length comprises:

obtaining a second x coordinate according to the first x coordinate, the second length, a sine value of the second polar angle and a cosine value of the second azimuth angle;

obtaining a second y coordinate according to the first y coordinate, the first x coordinate, the second x coordinate and a tangent value of the second azimuth angle;

obtaining a second z coordinate according to the first z coordinate, the second length and a cosine value of the second polar angle; and grouping the second x coordinate, the second y coordinate and the second z coordinate to form the set of coordinates of the second gravity sensor in the coordinate system.

12. The joint bending state determining method according to claim 9, wherein obtaining the joint angle according to the set of coordinates of the second gravity sensor in the coordinate system, the first length and the second length comprises:

obtaining a distance between an origin and the set of coordinates of the second gravity sensor in the coordinate system;

and obtaining the joint angle according to the distance between the origin and the set of coordinates of the second gravity sensor in the coordinate system, the first length, the second length and a cosine rule.

13. The joint bending state determining method according to claim 9, wherein obtaining the first length corresponding to the first gravity sensor and the second length corresponding to the second gravity sensor comprises:

determining that a predetermined axis of the first gravity sensor matches a gravity axis to ground, and accordingly determining that the first gravity sensor corresponds to the first length.

14. The joint bending state determining method according to claim 9, wherein obtaining the first length corresponding to the first gravity sensor and the second length corresponding to the second gravity sensor comprises:

by the first gravity sensor, determining that a predetermined axis of the first gravity sensor matches a gravity axis to ground, and generating a determined result; and determining that the first gravity sensor corresponds to the first length according to the determined result.

15. A joint bending state determining device, comprising:
a sensor group comprising:
a first gravity sensor configured to generate a first polar angle and a first azimuth angle;
and a second gravity sensor configured to generate a second polar angle and a second azimuth angle;
and a processor connected with the sensor group, and configured to obtain a first length corresponding to the first gravity sensor and a second length corresponding to the second gravity sensor, to obtain a set of coordinates of a joint in a coordinate system according to the first polar angle, the first azimuth angle and the first length, to obtain a set of coordinates of the second gravity sensor in the coordinate system according to the set of coordinates of the joint, the second polar angle, the second azimuth angle and the second length, and to obtain a joint angle by obtaining a distance between an origin and the set of coordinates of the second gravity sensor in the coordinate system, and obtaining the joint angle according to the distance between the origin and the set of coordinates of the second gravity sensor in the coordinate system, the first length, the second length and a cosine rule;

wherein the first length is associated with a distance between the first gravity sensor and the set of coordinates of the joint, and the second length is associated with a distance between the second gravity sensor and the set of coordinates of the joint;

and wherein the processor is further configured to obtain a first charge level of the first gravity sensor and a second charge level of the second gravity sensor, to control the first gravity sensor to capture the second polar angle and the second azimuth angle from the second gravity sensor and return the second polar angle and the second azimuth angle to the processor in response to determining that the first charge level is higher than the second charge level, and to control the second gravity sensor to capture the first polar angle and the first azimuth angle from the first gravity sensor and return the first polar angle and the first azimuth angle to the processor in response to determining that the first charge level is lower than the second charge level;

or wherein the first gravity sensor has the first charge level and is further configured to obtain the second charge level of the second gravity sensor, to capture the second polar angle and the second azimuth angle from the second gravity sensor and transmit the second polar angle and the second azimuth angle to the processor in response to determining that the first charge level is higher than the second charge level, and to transmit the first polar angle and the first azimuth angle to the second gravity sensor in response to determining that the first charge level is lower than the second charge level;

wherein the processor obtains the set of coordinates of the joint by obtaining a first x coordinate according to the first length, a sine value of the first polar angle and a cosine value of the first azimuth angle, obtaining a first y coordinate according to the first length, the sine value of the first polar angle and a sine value of the first azimuth angle, obtaining a first z coordinate according to the first length and a cosine value of the first polar angle, and grouping the first x coordinate, the first y coordinate and the first z coordinate to form the set of coordinates of the joint.

* * * * *